(12) United States Patent
Cabiri (10) Patent No.: US 7,967,795 B1
(45) Date of Patent: Jun. 28, 2011

(54) CARTRIDGE INTERFACE ASSEMBLY WITH DRIVING PLUNGER

(75) Inventor: Oz Cabiri, Macabim (IL)

(73) Assignee: LaModel Ltd., Or Yehuda (IL)

( * ) Notice: Subject to any disclaimer, the term of this patent is extended or adjusted under 35 U.S.C. 154(b) by 0 days.

(21) Appl. No.: 12/689,250

(22) Filed: Jan. 19, 2010

(51) Int. Cl.
*A61M 1/00* (2006.01)

(52) U.S. Cl. .................. 604/224; 604/155; 604/154

(58) Field of Classification Search .......... 604/207, 604/208, 224, 154, 155
See application file for complete search history.

(56) References Cited

U.S. PATENT DOCUMENTS

| | | |
|---|---|---|
| 1,795,630 A | 3/1931 | Wilson |
| 3,212,685 A | 10/1965 | Swan et al. |
| 4,195,636 A | 4/1980 | Behnke |
| 4,300,554 A | 11/1981 | Hessberg et al. |
| 4,403,987 A | 9/1983 | Gottinger |
| 4,435,173 A | 3/1984 | Siposs et al. |
| 4,599,082 A | 7/1986 | Grimard |
| 4,867,743 A | 9/1989 | Vaillancourt |
| 4,886,499 A | 12/1989 | Cirelli et al. |
| 5,109,850 A | 5/1992 | Blanco et al. |
| 5,190,521 A | 3/1993 | Hubbard et al. |
| 5,383,865 A | 1/1995 | Michel |
| 5,478,315 A | 12/1995 | Brothers et al. |
| 5,593,390 A | 1/1997 | Castellano et al. |
| 5,616,132 A | 4/1997 | Newman |
| 5,643,218 A | 7/1997 | Lynn et al. |
| 5,662,678 A | 9/1997 | Macklin |
| 5,690,618 A | 11/1997 | Smith et al. |
| 5,766,186 A | 6/1998 | Faraz et al. |
| 5,800,420 A | 9/1998 | Gross et al. |
| 5,807,375 A | 9/1998 | Gross et al. |
| 5,814,020 A | 9/1998 | Gross |
| 5,851,197 A | 12/1998 | Marano et al. |
| 5,858,001 A | 1/1999 | Tsals et al. |
| 5,931,814 A | 8/1999 | Alex et al. |
| 5,954,697 A | 9/1999 | Srisathapat et al. |
| 5,957,895 A | 9/1999 | Sage et al. |
| 5,968,011 A | 10/1999 | Larsen et al. |
| 6,074,369 A | 6/2000 | Sage et al. |
| 6,186,982 B1 | 2/2001 | Gross et al. |
| 6,200,289 B1 | 3/2001 | Hochman et al. |
| 6,200,296 B1 | 3/2001 | Dibiasi et al. |

(Continued)

FOREIGN PATENT DOCUMENTS

WO 9407553 A1 4/1994

(Continued)

OTHER PUBLICATIONS

Daikyo Crystal Zenitha polymer, Manufactured by Daikyo Seiko, Ltd.

(Continued)

*Primary Examiner* — Nicholas D Lucchesi
*Assistant Examiner* — Laura A Bouchelle
(74) *Attorney, Agent, or Firm* — Panitch Schwarze Belisario & Nadel LLP (57) ABSTRACT

A cartridge interface assembly including a driving plunger including an outer shaft, and a driver including an inner shaft, the inner shaft mating with an intermediate shaft, the intermediate shaft mating with the outer shaft, so that the shafts are movable telescopically with respect to one another, wherein rotation of the driver causes the driving plunger to advance in a direction away from the driver.

6 Claims, 5 Drawing Sheets

U.S. PATENT DOCUMENTS

| | | |
|---|---|---|
| 6,277,098 B1 | 8/2001 | Klitmose et al. |
| 6,277,099 B1 | 8/2001 | Strowe et al. |
| 6,287,283 B1 | 9/2001 | Ljunggreen et al. |
| 6,391,005 B1 | 5/2002 | Lum et al. |
| 6,485,461 B1 | 11/2002 | Mason et al. |
| 6,500,150 B1 | 12/2002 | Gross et al. |
| 6,503,231 B1 | 1/2003 | Prausnitz et al. |
| 6,517,517 B1 | 2/2003 | Farrugia et al. |
| 6,558,351 B1 | 5/2003 | Steil et al. |
| 6,589,229 B1 | 7/2003 | Connelly et al. |
| 6,595,956 B1 | 7/2003 | Gross et al. |
| 6,645,181 B1 | 11/2003 | Lavi et al. |
| 6,652,482 B2 | 11/2003 | Hochman |
| 6,656,158 B2 | 12/2003 | Mahoney et al. |
| 6,656,159 B2 | 12/2003 | Flaherty |
| 6,699,218 B2 | 3/2004 | Flaherty et al. |
| 6,743,211 B1 | 6/2004 | Prausnitz et al. |
| 6,749,587 B2 | 6/2004 | Flaherty |
| 6,768,425 B2 | 7/2004 | Flaherty et al. |
| 6,786,890 B2 | 9/2004 | Preuthun et al. |
| 6,805,687 B2 | 10/2004 | Dextradeur et al. |
| 6,824,529 B2 | 11/2004 | Gross et al. |
| 6,843,782 B2 | 1/2005 | Gross et al. |
| 6,854,620 B2 | 2/2005 | Ramey |
| 6,905,298 B1 | 6/2005 | Haring |
| 6,960,192 B1 | 11/2005 | Flaherty et al. |
| 7,001,360 B2 | 2/2006 | Veasey et al. |
| 7,060,054 B2 | 6/2006 | Nissels |
| 7,060,059 B2 | 6/2006 | Keith et al. |
| 7,128,727 B2 | 10/2006 | Flaherty et al. |
| 7,144,384 B2 | 12/2006 | Gorman et al. |
| 7,247,149 B2 | 7/2007 | Beyerlein |
| 7,250,037 B2 | 7/2007 | Shermer et al. |
| 7,291,159 B2 | 11/2007 | Schmelzeisen-Redeker et al. |
| 7,303,549 B2 | 12/2007 | Flaherty et al. |
| 7,390,314 B2 | 6/2008 | Stutz, Jr. et al. |
| 7,407,493 B2 | 8/2008 | Cane' |
| 7,455,663 B2 | 11/2008 | Bikovsky |
| 7,530,964 B2 | 5/2009 | Lavi et al. |
| 7,565,208 B2 | 7/2009 | Harris et al. |
| 7,569,050 B2 | 8/2009 | Moberg et al. |
| 7,585,287 B2 | 9/2009 | Bresina et al. |
| 7,588,559 B2 | 9/2009 | Aravena et al. |
| 7,628,770 B2 | 12/2009 | Ethelfeld |
| 7,637,891 B2 | 12/2009 | Wall |
| 7,641,649 B2 | 1/2010 | Moberg et al. |
| 7,678,079 B2 | 3/2010 | Shermer et al. |
| 7,686,787 B2 | 3/2010 | Moberg et al. |
| 7,699,829 B2 | 4/2010 | Harris et al. |
| 7,713,238 B2 | 5/2010 | Mernoe |
| 7,744,589 B2 | 6/2010 | Mounce et al. |
| 7,749,194 B2 | 7/2010 | Edwards et al. |
| 2001/0025168 A1 | 9/2001 | Gross et al. |
| 2001/0041869 A1 | 11/2001 | Causey et al. |
| 2002/0010423 A1 | 1/2002 | Gross et al. |
| 2002/0040208 A1 | 4/2002 | Flaherty et al. |
| 2002/0055711 A1 | 5/2002 | Lavi et al. |
| 2002/0123740 A1 | 9/2002 | Flaherty et al. |
| 2002/0169215 A1 | 11/2002 | Meng |
| 2003/0009133 A1 | 1/2003 | Ramey |
| 2003/0135159 A1 | 7/2003 | Daily et al. |
| 2003/0171717 A1 | 9/2003 | Farrugia et al. |
| 2004/0092873 A1* | 5/2004 | Moberg ............ 604/131 |
| 2004/0127857 A1 | 7/2004 | Shemesh et al. |
| 2004/0186419 A1 | 9/2004 | Cho |
| 2004/0260233 A1 | 12/2004 | Garibotto et al. |
| 2005/0033234 A1 | 2/2005 | Sadowski et al. |
| 2005/0065466 A1 | 3/2005 | Vedrine |
| 2005/0065472 A1 | 3/2005 | Cindrich et al. |
| 2005/0171512 A1 | 8/2005 | Flaherty |
| 2005/0197650 A1 | 9/2005 | Sugimoto et al. |
| 2005/0203461 A1 | 9/2005 | Flaherty et al. |
| 2005/0238507 A1 | 10/2005 | Dilanni et al. |
| 2005/0283114 A1 | 12/2005 | Bresina et al. |
| 2006/0095014 A1 | 5/2006 | Ethelfeld |
| 2006/0122577 A1 | 6/2006 | Poulsen et al. |
| 2006/0173406 A1 | 8/2006 | Hayes et al. |
| 2006/0173439 A1 | 8/2006 | Thorne et al. |
| 2006/0229569 A1 | 10/2006 | Lavi et al. |
| 2006/0264889 A1 | 11/2006 | Moberg et al. |
| 2006/0264890 A1 | 11/2006 | Moberg et al. |
| 2006/0264894 A1 | 11/2006 | Moberg et al. |
| 2006/0283465 A1 | 12/2006 | Nickel et al. |
| 2006/0293722 A1 | 12/2006 | Slatkine et al. |
| 2007/0021733 A1 | 1/2007 | Hansen et al. |
| 2007/0049865 A1 | 3/2007 | Radmer et al. |
| 2007/0073228 A1 | 3/2007 | Mernoe et al. |
| 2007/0118405 A1 | 5/2007 | Campbell et al. |
| 2007/0185449 A1 | 8/2007 | Mernoe |
| 2007/0203454 A1 | 8/2007 | Shermer et al. |
| 2008/0033367 A1 | 2/2008 | Haury et al. |
| 2008/0033369 A1 | 2/2008 | Kohlbrenner et al. |
| 2008/0051711 A1 | 2/2008 | Mounce et al. |
| 2008/0051730 A1 | 2/2008 | Bikovsky |
| 2008/0059133 A1 | 3/2008 | Edwards et al. |
| 2008/0097381 A1 | 4/2008 | Moberg et al. |
| 2008/0108951 A1 | 5/2008 | Jerde et al. |
| 2008/0140006 A1 | 6/2008 | Eskuri et al. |
| 2008/0140018 A1 | 6/2008 | Enggaard et al. |
| 2008/0188813 A1 | 8/2008 | Miller et al. |
| 2008/0215006 A1 | 9/2008 | Thorkild |
| 2008/0269723 A1 | 10/2008 | Mastrototaro et al. |
| 2008/0294143 A1 | 11/2008 | Tanaka et al. |
| 2008/0306449 A1 | 12/2008 | Kristensen et al. |
| 2008/0312601 A1 | 12/2008 | Cane |
| 2008/0319416 A1 | 12/2008 | Yodfat et al. |
| 2009/0054750 A1 | 2/2009 | Jennewine |
| 2009/0069784 A1 | 3/2009 | Estes et al. |
| 2009/0088731 A1 | 4/2009 | Campbell et al. |
| 2009/0093792 A1 | 4/2009 | Gross et al. |
| 2009/0093793 A1 | 4/2009 | Gross et al. |
| 2009/0124977 A1 | 5/2009 | Jensen |
| 2009/0143735 A1 | 6/2009 | De Polo et al. |
| 2009/0149830 A1 | 6/2009 | Spector |
| 2009/0182277 A1 | 7/2009 | Carter |
| 2009/0234319 A1 | 9/2009 | Marksteiner |
| 2009/0240240 A1 | 9/2009 | Hines et al. |
| 2009/0253973 A1 | 10/2009 | Bashan et al. |
| 2009/0259176 A1 | 10/2009 | Yairi |
| 2009/0326509 A1 | 12/2009 | Muse et al. |
| 2010/0030198 A1 | 2/2010 | Beebe et al. |
| 2010/0057057 A1 | 3/2010 | Hayter et al. |
| 2010/0076412 A1 | 3/2010 | Rush et al. |
| 2010/0094255 A1 | 4/2010 | Nycz et al. |
| 2010/0100076 A1 | 4/2010 | Rush et al. |
| 2010/0100077 A1 | 4/2010 | Rush et al. |
| 2010/0106098 A1 | 4/2010 | Atterbury et al. |
| 2010/0121314 A1 | 5/2010 | Iobbi |
| 2010/0145303 A1 | 6/2010 | Yodfat et al. |
| 2010/0162548 A1 | 7/2010 | Leidig |
| 2010/0168683 A1 | 7/2010 | Cabiri |
| 2010/0204657 A1 | 8/2010 | Yodfat et al. |
| 2010/0234830 A1 | 9/2010 | Straessler et al. |
| 2010/0274112 A1 | 10/2010 | Hoss et al. |
| 2010/0274192 A1 | 10/2010 | Mernoe |
| 2010/0280499 A1 | 11/2010 | Yodfat et al. |

FOREIGN PATENT DOCUMENTS

| | | |
|---|---|---|
| WO | 0202165 A2 | 1/2002 |
| WO | 2006037434 A1 | 4/2006 |
| WO | 2006069380 A1 | 6/2006 |
| WO | 2007051563 A1 | 5/2007 |
| WO | 2009044401 | 4/2009 |

OTHER PUBLICATIONS

Copaxonea, Manufactured by Teva Pharmaceutical Industries Ltd.
Int'l Search Report issued May 13, 2009 in Int'l Application No. PCT/IL2008/001312.
Int'l Preliminary Report on Patentability issued Apr. 7, 2010 in Int'l Application No. PCT/IL2008/001312; Written Opinion.
Int'l Search Report issued Apr. 26, 2010 in Int'l Application No. PCT/US2009/069552.
Office Action issued Apr. 5, 2010 in U.S. Appl. No. 12/244,666.
Office Action issued Sep. 21, 2010 in U.S. Appl. No. 12/244,666.
Office Action issued Apr. 5, 2010 in U.S. Appl. No. 12/244,688.
Office Action issued Sep. 2, 2010 in U.S. Appl. No. 12/244,688.

Office Action issued Sep. 30, 2010 in U.S. Appl. No. 12/689,250.
Int'l Search Report issued Jan. 12, 2011 in Int'l Application No. PCT/US2010/048556; Written Opinion.
U.S. Appl. No. 60/997,459, filed Oct. 2, 2007.
U.S. Appl. No. 12/559,563, filed Sep. 15, 2009.
U.S. Appl. No. 12/689,249, filed Jan. 19, 2010.

* cited by examiner

CARTRIDGE INTERFACE ASSEMBLY WITH DRIVING PLUNGER

FIELD OF THE INVENTION

The present invention generally relates to external drug pumps, and particularly to an assembly for pushing a drug from a cartridge, in which the assembly interfaces between an actuator, e.g., a motor, and a pushing device, e.g., a plunger in the cartridge.

BACKGROUND OF THE INVENTION

External drug pumps are typically used to deliver to patients substances which contain large molecules which cannot be digested when administered orally, such as insulin, biogenic drugs or protein drugs among others. Typically, the pump is adhered to the abdomen or chest of the patient and delivers the substance to the patient via a cannula or needle that is inserted into the patient's skin.

PCT Patent Application PCT/IL2008/001312 (published as WO 2009/044401) to Gross and Cabiri (as well as U.S. patent application Ser. Nos. 12/244,666 and 12/244,668, the disclosures of which are incorporated herein by reference), describes an external drug pump. In this pump, a vial is provided that contains a substance to be administered to a subject. (The terms "drug" and "substance" are used interchangeably throughout the specification and claims, and encompass any material administered to a subject. The term "cartridge" throughout the specification and claims encompasses any container for a drug, such as but not limited to, a cartridge, vial, syringe, bottle, ampoule and many more, and is not limited to any size or shape.)

The cartridge is sealed by a stopper, and has first and second threaded elements (e.g., a screw and a nut) that are threadedly coupled to each other. The distal end of the second threaded element defines a coupling portion that couples the second threaded element to the stopper. The first threaded element is rotatable with respect to the cartridge, and is linearly immobile with respect to the cartridge during rotation of the first threaded element. The first threaded element, rotated by a motor, is configured to linearly advance the stopper and at least the distal end of the second threaded element toward the distal end of the cartridge, without substantially rotating the second threaded element and the stopper.

The following is provided to facilitate understanding of the above described assembly.

Figure 1:
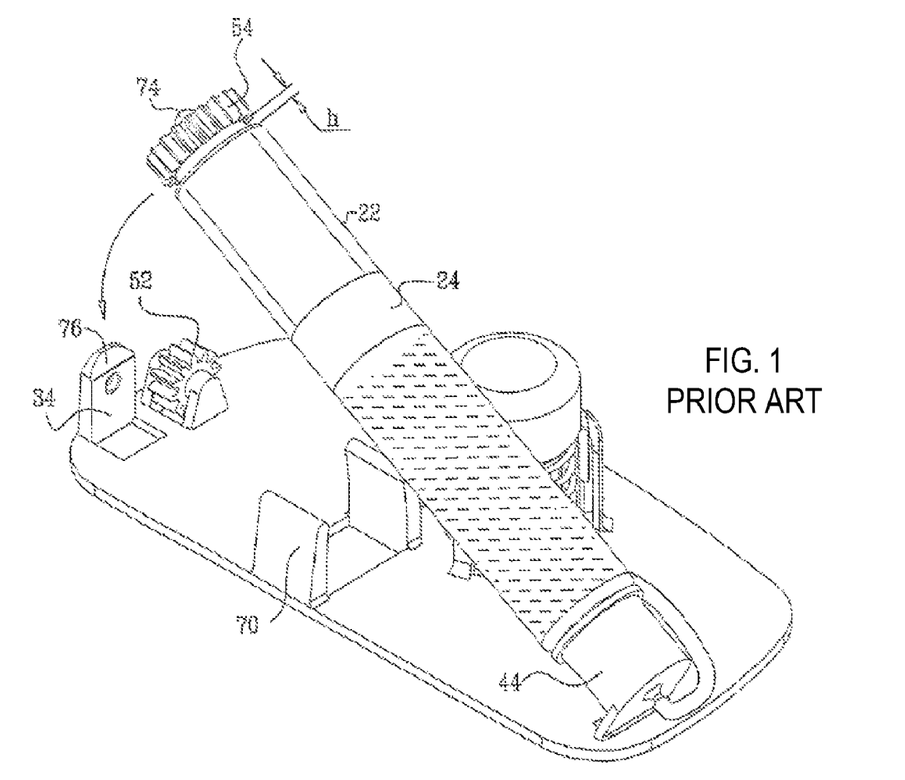
FIG. 1 is a simplified illustration of a prior art cartridge assembly.

Reference is made to FIG. 1, which illustrates the relevant elements of the prior art cartridge assembly of WO 2009/044401 (based on FIG. 4 of that application), wherein a cartridge 22 is inserted into a housing base.

The distal end of cartridge 22 is inserted into a cartridge piercing mechanism 44, which pierces a seal at the distal end of cartridge 22 having a stopper 24 therein (the stopper being an example of a plunger, piston or pushing device; the stopper will also be referred to as a plunger). Cartridge 22 is then lowered into the housing base. Typically, opposing resilient arms 70 support the cartridge upon the housing base. As cartridge 22 is lowered into the housing base, a first cog 52 engages a second cog 54. (First cog 52 is rotated by the motor, not shown here.) In some applications, before insertion of cartridge 22 into the housing, first threaded element 26 protrudes a distance h from the proximal end of the cartridge. The proximal end of the first threaded element (or of second cog 54) comprises a rounded portion 74. Portion 34 of the housing base comprises an angled face 76. As rounded portion 74 slides past the angled face, the first threaded element is pushed the distance h inside the cartridge. As a result, the first and second threaded elements 26 and 28 and the stopper 24 are displaced towards the distal end of the cartridge 22. During operation, the motor (not shown) turns cog 52, which turns cog 54. This linearly advances stopper 24 towards the distal end of the cartridge 22, thereby administering the substance from cartridge 22.

Figure 2:
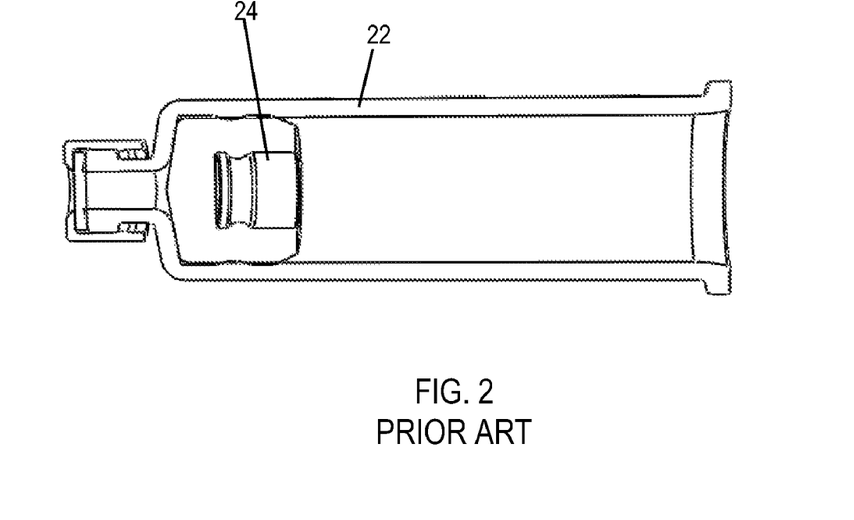
FIG. 2 is a simplified illustration of the prior art cartridge with plunger in an initial position before the cartridge has been filled.
Figure 3:
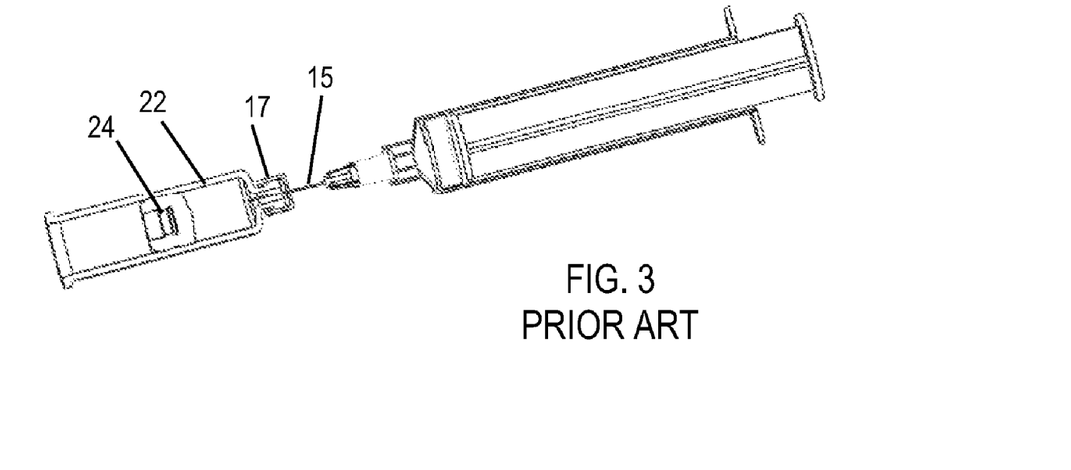
FIG. 3 is a simplified illustration of filling the prior art cartridge with a hypodermic needle inserted through a septum in the cartridge.
Figure 4:
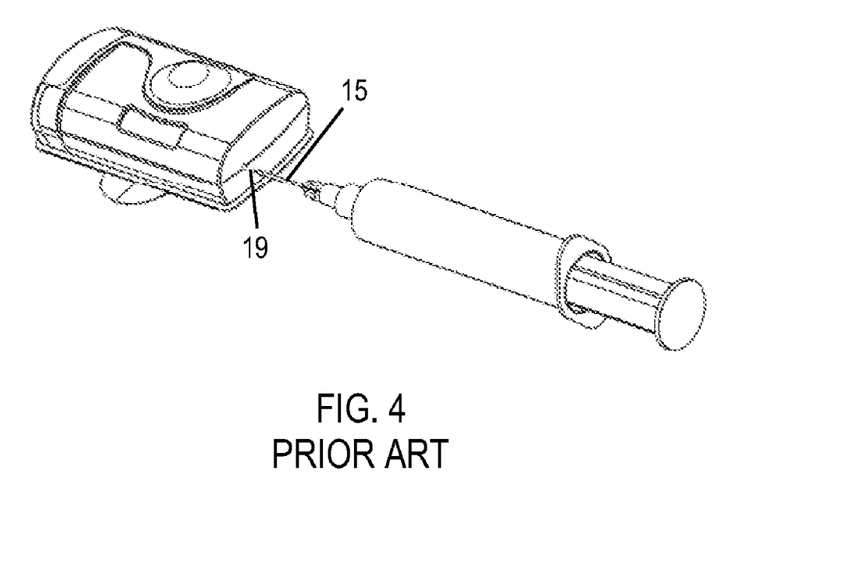
FIG. 4 is a simplified illustration of filling the prior art cartridge with a hypodermic needle inserted through a septum in a housing of a drug pump.

Reference is now made to FIG. 2, which illustrates cartridge 22 with plunger 24 in an initial position before cartridge 22 has been filled. The cartridge is either pre-filled by the manufacturer or filled by the user, such as with a hypodermic needle 15 inserted through a septum 17 in cartridge 22 (FIG. 3) or through a septum 19 in the housing of the drug pump (FIG. 4). As shown in FIG. 3, the plunger 24 moves linearly in the cartridge 22 as the cartridge is filled. Because no two cartridges will be filled with exactly the same amount of substance, such as due to tolerances, different injected volumes, different diameters or other dimensions, different plunger shapes, air bubbles or other factors, there is unfortunately no definitive position of the plunger 24 after cartridge 22 has been filled. This can cause a problem because it is possible that the overall length of the geared and threaded mechanism (which is predefined) that interfaces with plunger 24 may not meet the filled position of plunger 24 (which is unknown), thereby causing a problem to properly push against plunger 24 in order to administer the substance.

SUMMARY OF THE INVENTION

The present invention seeks to provide an improved assembly for pushing a drug from a cartridge, in which the assembly interfaces between an actuator, e.g., a motor, and a pushing device, e.g., a plunger in the cartridge, as is described more in detail hereinbelow. The invention solves the above mentioned problem of the prior art. Although the invention is described with reference to PCT Patent Application WO 2009/044401, nevertheless it is understood that the invention is applicable for many types of motor-driven drug cartridges.

There is thus provided in accordance with an embodiment of the present invention a cartridge interface assembly including a driving plunger including an outer shaft, and a driver including an inner shaft, the inner shaft mating with an intermediate shaft, the intermediate shaft mating with the outer shaft, so that the shafts are movable telescopically with respect to one another, wherein rotation of the driver causes the driving plunger to advance in a direction away from the driver. The driver may include a gear wheel.

In accordance with a non-limiting embodiment of the present invention the inner shaft is threadedly received inside a hollow portion of the intermediate shaft, and the intermediate shaft is threadedly received inside a hollow portion of the outer shaft.

In accordance with an embodiment of the present invention the cartridge interface assembly is inserted in a cartridge in which a plunger is slidingly disposed, and rotation of the driver causes the driving plunger to advance distally in the cartridge until abutting the plunger.

There is also provided in accordance with an embodiment of the present invention a method for interfacing between a driver and a plunger slidingly disposed in a cartridge, the method including inserting a cartridge interface assembly in the cartridge, the cartridge interface assembly including a driving plunger including an outer shaft, and a driver including an inner shaft, the inner shaft mating with an intermediate shaft, the intermediate shaft mating with the outer shaft, so that the shafts are movable telescopically with respect to one another, and rotating the driver to cause the driving plunger to advance distally in the cartridge until abutting the plunger.

BRIEF DESCRIPTION OF THE DRAWINGS

The present invention will be understood and appreciated more fully from the following detailed description taken in conjunction with the drawings in which.

DETAILED DESCRIPTION OF EMBODIMENTS

Figure 5:
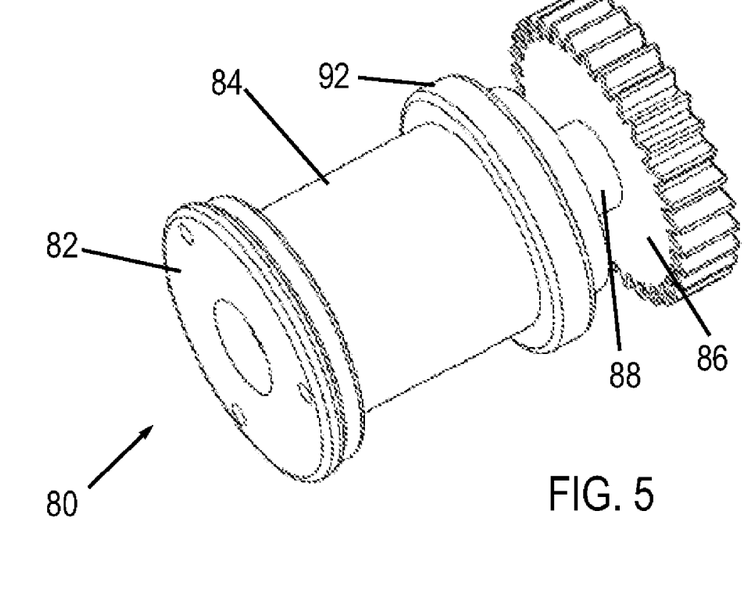
FIGS. 5 and 6 are simplified pictorial and sectional illustrations, respectively, of a cartridge interface assembly including a driving plunger, constructed and operative in accordance with an embodiment of the present invention.
Figure 6:
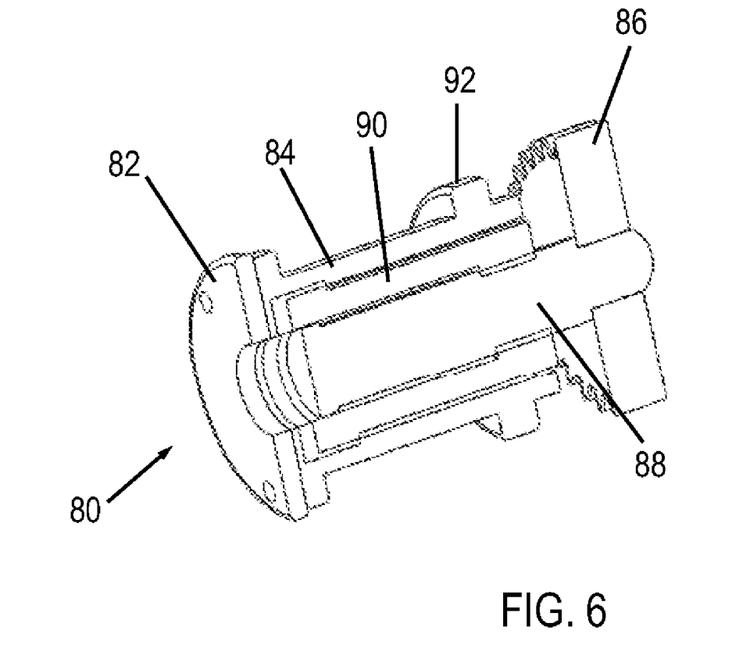

Reference is now made to FIGS. 5 and 6, which illustrate a cartridge interface assembly 80, constructed and operative in accordance with a non-limiting embodiment of the present invention.

Cartridge interface assembly 80 includes a driving plunger 82 at the distal end of an outer shaft 84. A driver 86, such as but not limited to, a gear wheel, includes an inner shaft 88. Inner shaft 88 is received inside a hollow portion of an intermediate shaft 90 and threadedly mates therewith. Intermediate shaft 90 is in turn received inside a hollow portion of outer shaft 84 and threadedly mates therewith. The shafts 84, 88 and 90 are arranged to move telescopically with respect to one another. Outer shaft 84 may further include a proximal O-ring 92. The driving plunger 82 and O-ring 92 are preferably made of an elastomer, such as natural or synthetic rubber. The other parts may be made of plastic or metal.

Figure 7:
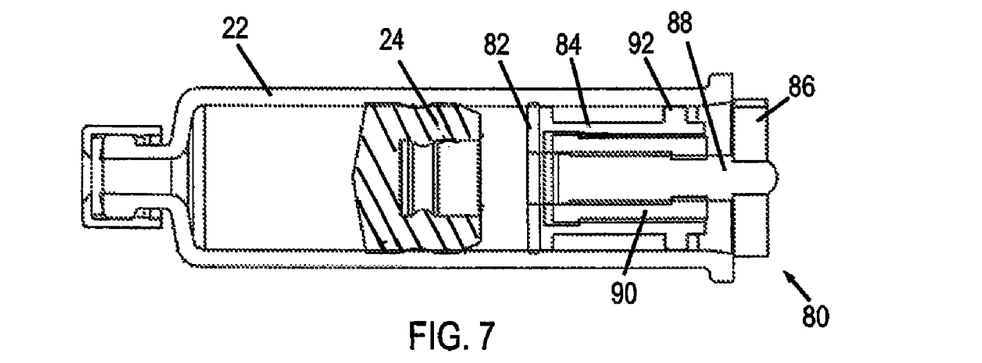
FIGS. 7 and 8 are simplified illustrations of the cartridge interface assembly inserted in a cartridge, respectively before and after the driving plunger abuts against the plunger of the cartridge, in accordance with an embodiment of the present invention.

Reference is now made to FIG. 7, which illustrates the cartridge interface assembly 80 inserted in cartridge 22. Driving plunger 82 is initially distanced somewhat from plunger 24 of cartridge 22. Rotation of driver 86 (such as by meshing with a rotating motor not shown) causes inner shaft 88 to rotate, which causes intermediate shaft 90 to rotate and advance linearly towards the distal end of cartridge interface assembly 80, that is, in the direction towards plunger 24 as indicated by arrow 91. The distal movement of intermediate shaft 90 in turn causes outer shaft 84 to advance distally together with driving plunger 82. The friction of driving plunger 82 against the inner wall of cartridge 22 is such that it is much easier for driving plunger 82 to move linearly than to rotate, such that the rotation of inner shaft 88 and intermediate shaft 90 cause driving plunger 82 to advance distally in cartridge 22 until driving plunger 82 abuts against plunger 24 as shown in FIG. 8, which shows the plunger 24 in a more distal position than its initial position shown in FIG. 7.

Figure 8:
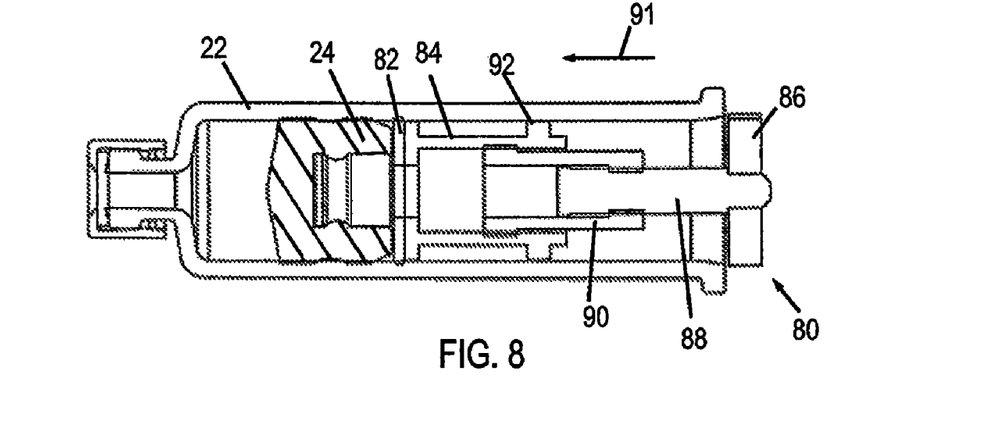
Figure 9:
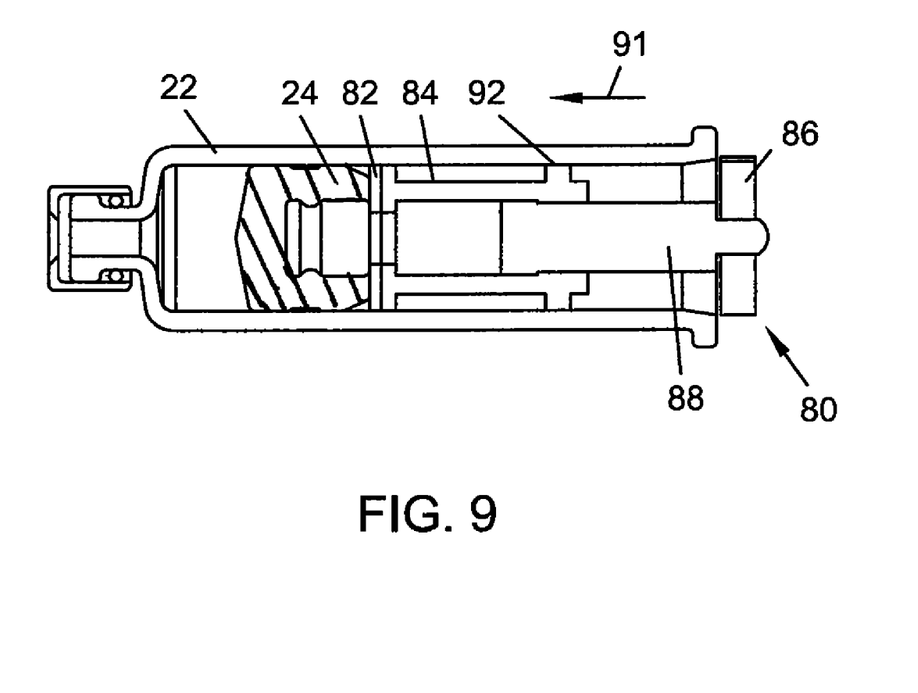
FIG. 9 is a simplified illustration of the cartridge interface assembly inserted in a cartridge, after the driving plunger abuts against the plunger of the cartridge, in accordance with an alternate embodiment of the present invention.

FIG. 9 shows an alternate embodiment from what is shown in FIG. 8. The only difference between the embodiments shown in FIGS. 8 and 9, is that the intermediate shaft 90 is omitted and the inner shaft 88 and the outer shaft 84 are directly threadedly mated together.

Thus, with the present invention, no matter what the final position of plunger 24 is after filling cartridge 22 with the substance to be administered, the driving mechanism for pushing plunger 24 will always properly contact plunger 24 via cartridge interface assembly 80 due to the distance compensating action of cartridge interface assembly 80.

It will be appreciated by persons skilled in the art that the present invention is not limited by what has been particularly shown and described hereinabove. Rather the scope of the present invention includes both combinations and subcombinations of the features described hereinabove as well as modifications and variations thereof which would occur to a person of skill in the art upon reading the foregoing description and which are not in the prior art.

What is claimed is:

1. A combination cartridge and cartridge interface assembly comprising:
a rotationally immobile cartridge having an inner cylindrical surface, a first stopper slidingly inserted in the cartridge, a distal end and a substance therein for administration to a subject;
a cartridge interface assembly comprising:
a driving plunger comprising a first shaft; and
a driver comprising a second shaft, said second shaft mating with said first shaft, so that said shafts are movable telescopically with respect to one another, wherein rotation of said driver causes said driving plunger to linearly advance in a direction away from said driver, the arrangement being such that on insertion of the cartridge interface assembly in the rotationally immobile cartridge, the driving plunger is in complementary anti-rotation friction relation with the inner cylindrical surface, said complementary anti-rotation friction relation being the only force impeding rotation of the driving plunger with respect to the cartridge such that rotation of said driver causes said driving plunger to linearly advance only towards the distal end until the driving plunger abuts against the stopper whereupon the driving plunger urges the stopper towards the distal end for metering substance from the cartridge.

2. The combination according to claim 1, wherein said driver comprises a gear wheel.

3. The combination according to claim 1, wherein said second shaft is threadedly received inside a hollow portion of said first shaft.

4. The combination according to claim 1, further including an intermediate shaft threadedly received inside a hollow portion of said first shaft, said second shaft being threadedly received inside a hollow portion of said intermediate shaft.

5. The combination according to claim 1, wherein said driving plunger is at a distal end of said first shaft.

6. A method for interfacing between a driver and plunger slidingly disposed in a rotationally immobile cartridge, the method comprising:
providing a rotationally immobile cartridge having an inner cylindrical surface, a first stopper slidingly inserted in the cartridge, a distal end and a substance therein for administration to a subject inserting a cartridge interface assembly in the rotationally immobile cartridge, said cartridge interface assembly comprising a driving plunger comprising a first shaft, and a driver comprising a second shaft, said second shaft mating with said first shaft, so that said shafts are moveable telescopically with respect to one another; and rotating said driver to cause said driving plunger to linearly advance distally in said cartridge until abutting said plunger, the arrangement being such that on insertion of the cartridge interface assembly in the rotationally immobile cartridge, the driving plunger is in complementary anti-rotation friction relation with the inner cylindrical surface, said complementary sealing anti-rotation friction relation being the only force impeding rotation of the driving plunger with respect to the cartridge such that rotation of said driver causes said driving plunger to linearly advance only towards the distal end until the driving plunger abuts against the stopper whereupon the driving plunger urges the stopper towards the distal end for metering substance from the cartridge.

* * * * *

UNITED STATES PATENT AND TRADEMARK OFFICE
CERTIFICATE OF CORRECTION

| | | |
|---|---|---|
| PATENT NO. | : 7,967,795 B1 | Page 1 of 1 |
| APPLICATION NO. | : 12/689250 | |
| DATED | : June 28, 2011 | |
| INVENTOR(S) | : Oz Cabiri | |

It is certified that error appears in the above-identified patent and that said Letters Patent is hereby corrected as shown below:

In the Claims

Column 4 line 61 thru Column 6 line 9 Claim 6 should read:
6. A method for interfacing between a driver and plunger slidingly disposed in a rotationally immobile cartridge, the method comprising:

providing a rotationally immobile cartridge having an inner cylindrical surface, a first stopper slidingly inserted in the cartridge, a distal end and a substance therein for administration to a subject inserting a cartridge interface assembly in the rotationally immobile cartridge, said cartridge interface assembly comprising a driving plunger comprising a first shaft, and a driver comprising a second shaft, said second shaft mating with said first shaft, so that said shafts are moveable telescopically with respect to one another; and rotating said driver to cause said driving plunger to linearly advance distally in said cartridge until abutting said first stopper, the arrangement being such that on insertion of the cartridge interface assembly in the rotationally immobile cartridge, the driving plunger is in complementary anti-rotation friction relation with the inner cylindrical surface, said complementary sealing anti-rotation friction relation being the only force impeding rotation of the driving plunger with respect to the cartridge such that rotation of said driver causes said driving plunger to linearly advance only towards the distal end until the driving plunger abuts against the first stopper whereupon the driving plunger urges the first stopper towards the distal end for metering substance from the cartridge.

Signed and Sealed this
Twenty-ninth Day of September, 2015

Michelle K. Lee
*Director of the United States Patent and Trademark Office*